US00PP26266P2

(12) United States Plant Patent
Kumar

(10) Patent No.: US PP26,266 P2
(45) Date of Patent: Dec. 22, 2015

(54) ***CORDYLINE* PLANT NAMED 'SPRILECFIRE'**

(50) Latin Name: ***Cordyline* hybrid**
Varietal Denomination: Sprilecfire

(71) Applicant: Krishna Bhuvanendra Kumar, Zhejiang (CN)

(72) Inventor: Krishna Bhuvanendra Kumar, Zhejiang (CN)

(73) Assignee: Sprint Horticulture PTY. LTD., Wamberal, NSW (AU)

( * ) Notice: Subject to any disclaimer, the term of this patent is extended or adjusted under 35 U.S.C. 154(b) by 153 days.

(21) Appl. No.: 13/999,010

(22) Filed: Dec. 31, 2013

(51) Int. Cl.
*A01H 5/12* (2006.01)

(52) U.S. Cl.
USPC ..... Plt./383

(58) Field of Classification Search
USPC ..... Plt./383
See application file for complete search history.

*Primary Examiner* — Susan McCormick Ewoldt
(74) *Attorney, Agent, or Firm* — C. A. Whealy

(57) ABSTRACT

A new and distinct cultivar of *Cordyline* plant named 'Sprilecfire', characterized by its relatively tall, broad and upright plant habit and leaves initially erect to outwardly arching and slightly recurving; moderately vigorous to vigorous growth habit; long lanceolate variegated leaves with red purple and dark greyed purple-colored longitudinal stripes; and excellent keeping quality and good garden performance.

2 Drawing Sheets

Botanical designation: *Cordyline* hybrid.
Cultivar denomination: 'SPRILECFIRE'.

BACKGROUND OF THE INVENTION

The present invention relates to a new and distinct *Cordyline* plant, botanically known as *Cordyline* hybrid and hereinafter referred to by the name 'Sprilecfire'.

The new *Cordyline* plant is a naturally-occurring whole plant mutation of a proprietary selection of *Cordyline* hybrid identified as code number CBZ67, not patented. The new *Cordyline* plant was discovered and selected by the Inventor from within a population of plants of the parent selection in a controlled laboratory environment in Zhejiang, China in November, 2004.

Asexual reproduction of the new *Cordyline* plant by micropropagated cuttings in Zhejiang, China since November, 2004 has shown that the unique features of this new *Cordyline* plant are stable and reproduced true to type in successive generations.

SUMMARY OF THE INVENTION

Plants of the new *Cordyline* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Sprilecfire'. These characteristics in combination distinguish 'Sprilecfire' as a new and distinct *Cordyline* plant:

1. Relatively tall, broad and upright plant habit with leaves initially erect to outwardly arching and slightly recurving.
2. Moderately vigorous to vigorous growth habit.
3. Long lanceolate variegated leaves with red purple and dark greyed purple-colored longitudinal stripes.
4. Excellent keeping quality and good garden performance.

Plants of the new *Cordyline* differ primarily from plants of the parent selection in leaf color as plants of the parent selection have purple-colored leaves.

Plants of the new *Cordyline* can be compared to plants of the *Cordyline australis* 'Purple Sensation', not patented. In side-by-side comparisons conducted in Mangrove Mountain, New South Wales, Australia, plants of the new *Cordyline* differed primarily from plants of 'Purple Sensation' in the following characteristics:

1. Plants of the new *Cordyline* were not branched whereas plants of 'Purple Sensation' were branched.
2. Leaves of plants of the new *Cordyline* and 'Purple Sensation' differed in color as plants of 'Purple Sensation' had greyed red and brown-colored leaves.

Plants of the new *Cordyline* can also be compared to plants of the *Cordyline banksii* 'Sprilecpink', disclosed in U.S. Plant Pat. No. 19,213. In side-by-side comparisons conducted in Mangrove Mountain, New South Wales, Australia, plants of the new *Cordyline* differed primarily from plants of the 'Sprilecpink' in the following characteristics:

1. Plants of the new *Cordyline* were taller and broader than plants of 'Sprilecpink'.
2. Plants of the new *Cordyline* had longer leaves than plants of 'Sprilecpink'.
3. Plants of the new *Cordyline* and 'Sprilecpink' differed in leaf color as plants of 'Sprilecpink' had red purple, greyed purple and brown-colored leaves.

BRIEF DESCRIPTION OF THE PHOTOGRAPHS

The accompanying photographs illustrate the overall appearance of the new *Cordyline* plant showing the colors as true as it is reasonably possible to obtain in colored reproductions of this type. Colors in the photographs may differ slightly from the color values cited in the detailed botanical description which accurately describe the colors of the new *Cordyline* plant.

The photograph on the first sheet comprises side perspective view of a typical plant of 'Sprilecfire' grown in a container.

The photograph on the second sheet is a close-up view of a typical plant of 'Sprilecfire' grown in container.

DETAILED BOTANICAL DESCRIPTION

The aforementioned photographs and following observations and measurements describe plants grown during the spring, summer and autumn in 17.5-cm containers in an outdoor nursery in Mangrove Mountain, New South Wales, Australia and under cultural practices typical of commercial *Cordyline* plant production. During the production of the plants, day temperatures ranged from 20° C. to 30° C., night temperatures ranged from 15° C. to 22° C. and light levels ranged from 7,500 to 8,400 foot-candles. Plants were ten months old when the photographs were taken and nine months old when the botanical description was taken. In the following description, color references are made to The Royal Horticultural Society Colour Chart, 2001 Edition, except where general terms of ordinary dictionary significance are used.

Botanical classification: *Cordyline* hybrid 'Sprilecfire'.

Parentage: Naturally-occurring whole plant mutation of proprietary selection of *Cordyline* hybrid identified as code number CBZ67, not patented.

Propagation:

- *Type*.—By micropropagated cuttings.
- *Time to initiate roots, summer*.—About two weeks at temperatures ranging from 25° C. to 35° C.
- *Time to initiate roots, winter*.—About three weeks at temperatures about 18° C.
- *Time to produce a rooted young plant, summer*.—About one to two months at temperatures about 25° C.
- *Time to produce a rooted young plant, winter*.—About two months at temperatures about 18° C.
- *Root description*.—Medium thickness, fleshy; white in color.
- *Rooting habit*.—Freely branching; dense.

Plant description:

- *Plant and growth habit*.—Relatively tall and broad with upright plant habit and leaves initially erect to outwardly arching and slightly recurving; non-branching habit; moderately vigorous to vigorous growth habit; moderate to fast growth rate.
- *Plant height*.—About 77 cm to 99 cm.
- *Plant diameter or spread*.—About 95 cm to 127 cm.

Leaf description:

- *Arrangement*.—Whorled; sessile.
- *Length*.—About 73 cm to 90 cm.
- *Width*.—About 2 cm to 2.5 cm.
- *Shape*.—Lanceolate.
- *Apex*.—Acute.
- *Margin*.—Entire.
- *Cross-sectional profile*.—Towards the base, concave, flattening towards the middle of the leaf to the apex.
- *Texture, upper and lower surfaces*.—Leathery; corrugated; glabrous.
- *Luster, upper and lower surfaces*.—Slightly glossy.
- *Venation pattern*.—Parallel.
- *Color*.—Developing leaves, upper surface: Longitudinal stripes, close to 200A and 185A. Developing leaves, lower surface: Close to 200A. Fully expanded leaves, upper surface: Longitudinal stripes, close to 60A and 187A. Fully expanded leaves, lower surface: Close to 200A. Venation, upper and lower surfaces: Similar to surface coloration.

Flower description: Flower initiation and development has not been observed on plants of the new *Cordyline*.

- *Disease & pest resistance*.—Plants of the new *Cordyline* have not been shown to be resistant to pathogens and pests common to *Cordyline* plants.
- *Keeping quality*.—Excellent keeping quality; plants of the new *Cordyline* are durable and will maintain good leaf substance indefinitely.
- *Garden performance*.—Plants of the new *Cordyline* have been observed to have good garden performance and to tolerate wind, rain, full sunlight and temperatures ranging from about 5° C. to about 45° C.

It is claimed:

1. A new and distinct *Cordyline* plant named 'Sprilecfire' as illustrated and described.

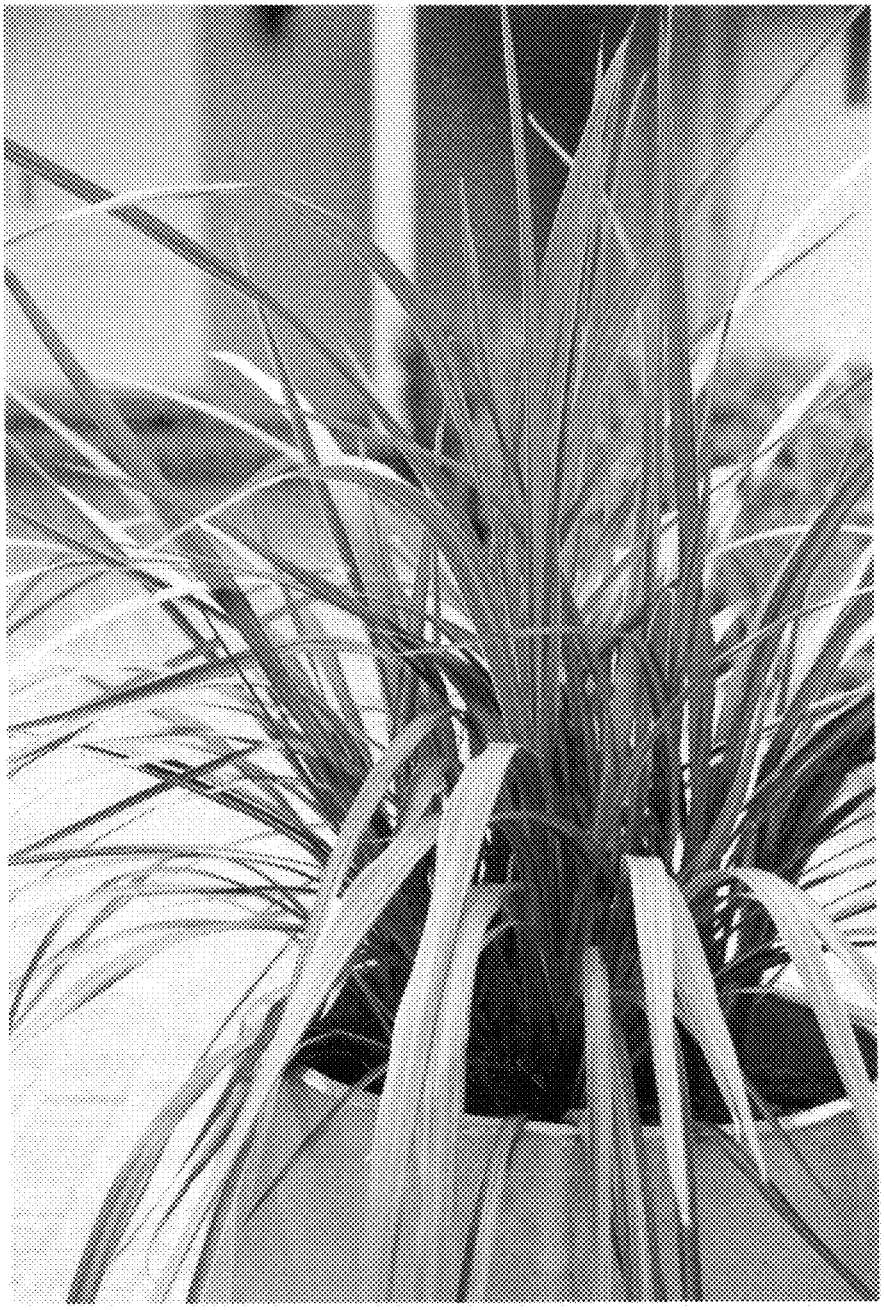

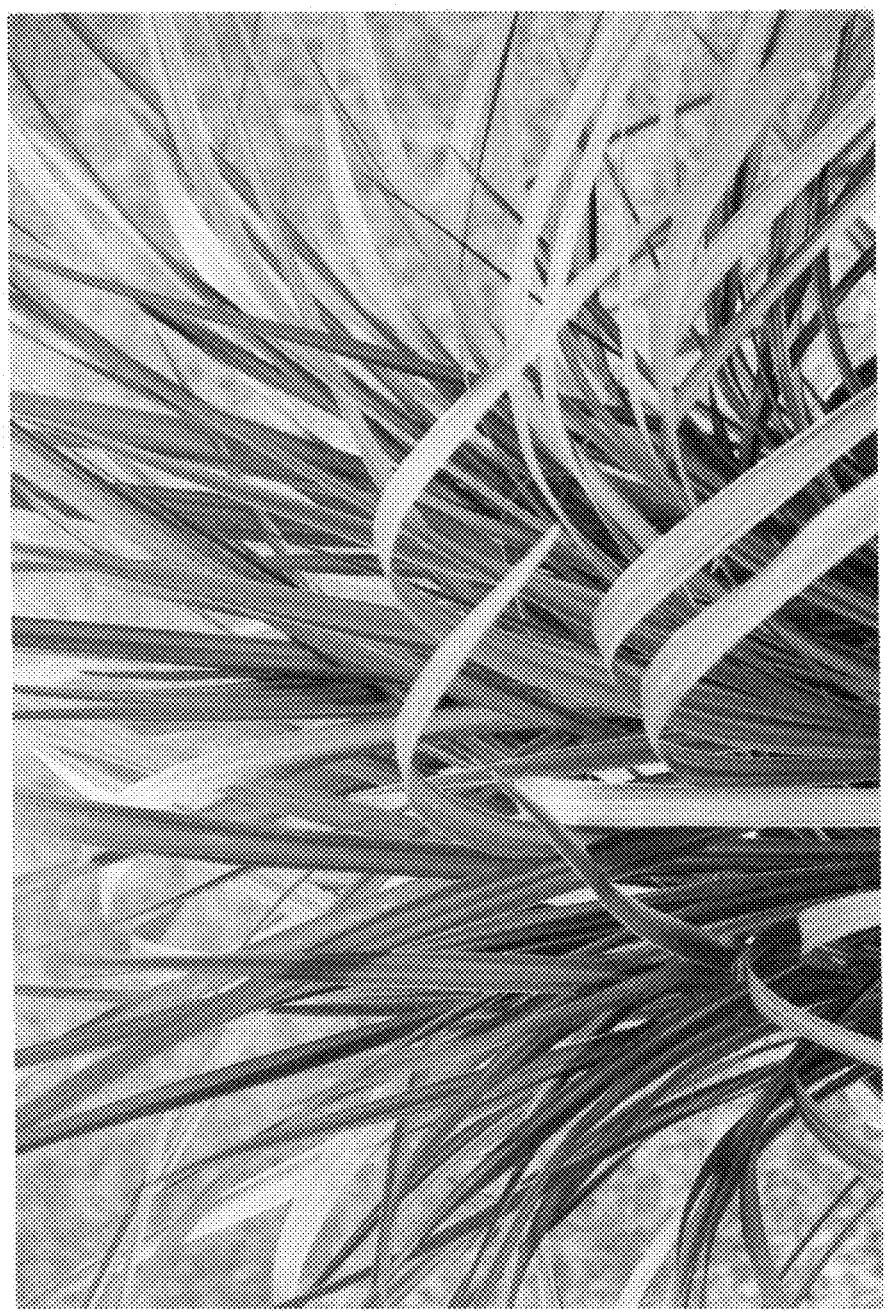

* * * * *